United States Patent [19]

Odermatt et al.

[11] Patent Number: 5,341,622
[45] Date of Patent: Aug. 30, 1994

[54] METHOD OF FOLDING OF PACK FOR HOLDING SUTURE MATERIAL

[75] Inventors: Erich Odermatt; Robert Sulzberger, both of Schaffhausen, Switzerland

[73] Assignee: B. Braun SSC AG, Emmenbrueke, Switzerland

[21] Appl. No.: 118,228

[22] Filed: Sep. 9, 1993

Related U.S. Application Data

[62] Division of Ser. No. 897,276, Jun. 11, 1992, Pat. No. 5,271,494.

[30] Foreign Application Priority Data

Jun. 11, 1991 [EP] European Pat. Off. ........ 91109584.2

[51] Int. Cl.$^5$ ..................... B65B 63/04; B65B 11/58
[52] U.S. Cl. ............................ 53/429; 53/449; 53/462; 206/63.3; 206/388
[58] Field of Search ............... 53/410, 429, 449, 462, 53/133.1, 207; 206/63.3, 227, 380, 382, 388, 495

[56] References Cited

U.S. PATENT DOCUMENTS

| 3,136,418 | 6/1964 | Stacy et al. | 206/63.3 |
| 3,206,018 | 9/1965 | Lewis et al. | 206/63.3 |
| 3,869,044 | 3/1975 | Olsson et al. | 206/63.3 |
| 4,089,410 | 5/1978 | Bolanowski et al. | 206/63.3 |
| 4,120,395 | 10/1978 | Mandel et al. | 206/63.3 |
| 4,126,221 | 11/1978 | Cerwin | 206/63.3 |
| 4,253,563 | 3/1981 | Komarnycky | 206/63.3 |
| 4,406,363 | 9/1983 | Aday | 206/63.3 |
| 4,491,218 | 1/1985 | Aday | 206/63.3 |
| 4,700,833 | 10/1987 | Smith | 206/380 |
| 4,884,681 | 12/1989 | Roshdy et al. | 206/63.3 |

FOREIGN PATENT DOCUMENTS

| 2532992 | 2/1976 | Fed. Rep. of Germany . | |
| 2332359 | 11/1975 | France | 206/63.3 |

*Primary Examiner*—Bryon P. Gehman
*Attorney, Agent, or Firm*—Spensley Horn Jubas & Lubitz

[57] ABSTRACT

A suture material pack for surgical suture material. The pack includes a folding card with a base plate and a pair of cover plates adjoining the same in the longitudinal direction. Projecting to one side from the base plate, there is a first holding plate over which a second holding plate may be folded. The holding plates enclose the suture material and they are shorter than the suture material loop. During the placing of the suture material and the closing of the holding plates, the suture material loop can be held at the ends. The cover plates and are then folded onto the base plate and the holding plate folded thereon so that the suture material is protected. The folding card is welded into a foil sheath that is torn open to take out the filament. In doing so, a flap provided at the second cover plate is torn off so as to expose the filament end.

7 Claims, 2 Drawing Sheets

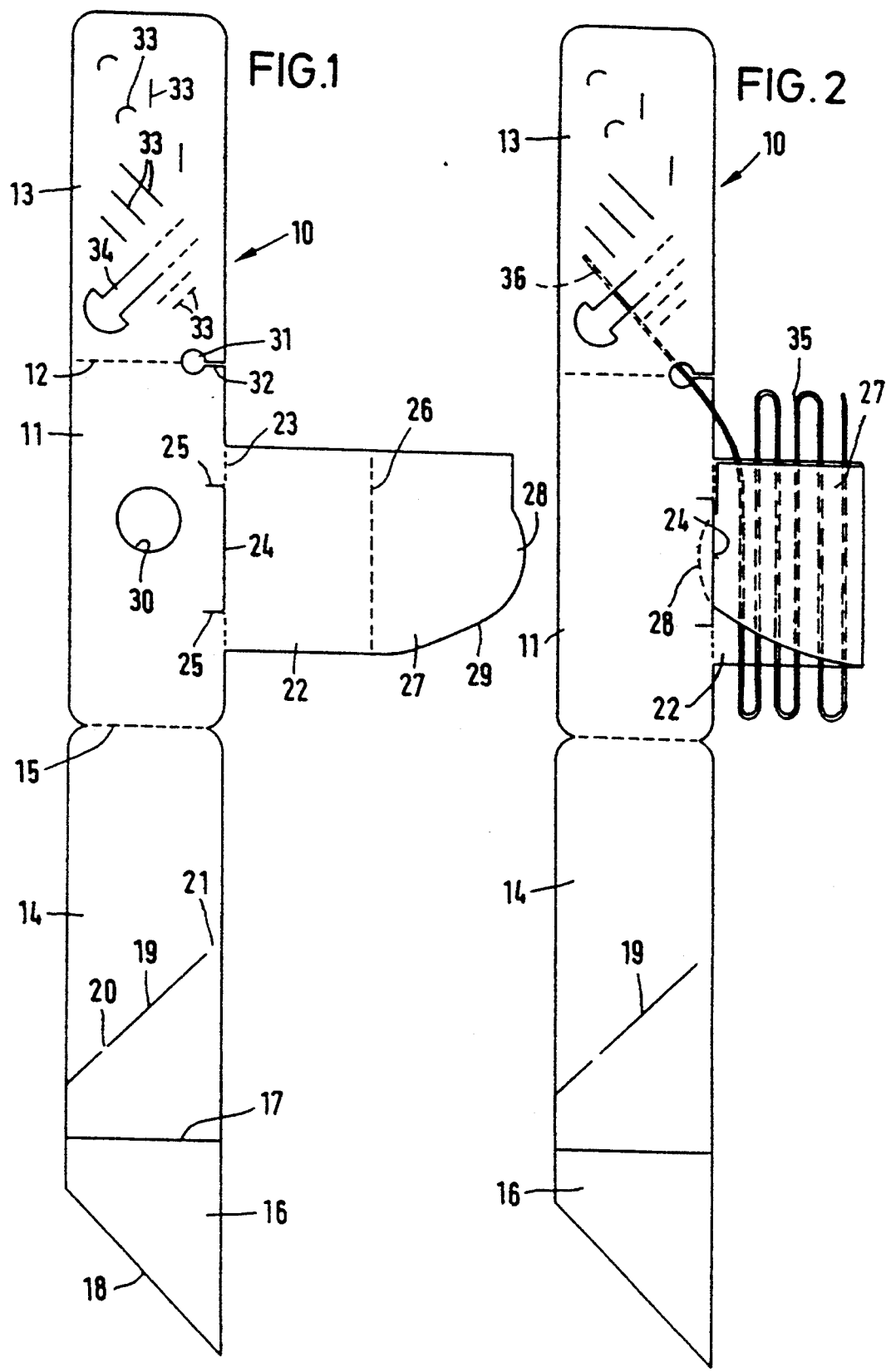

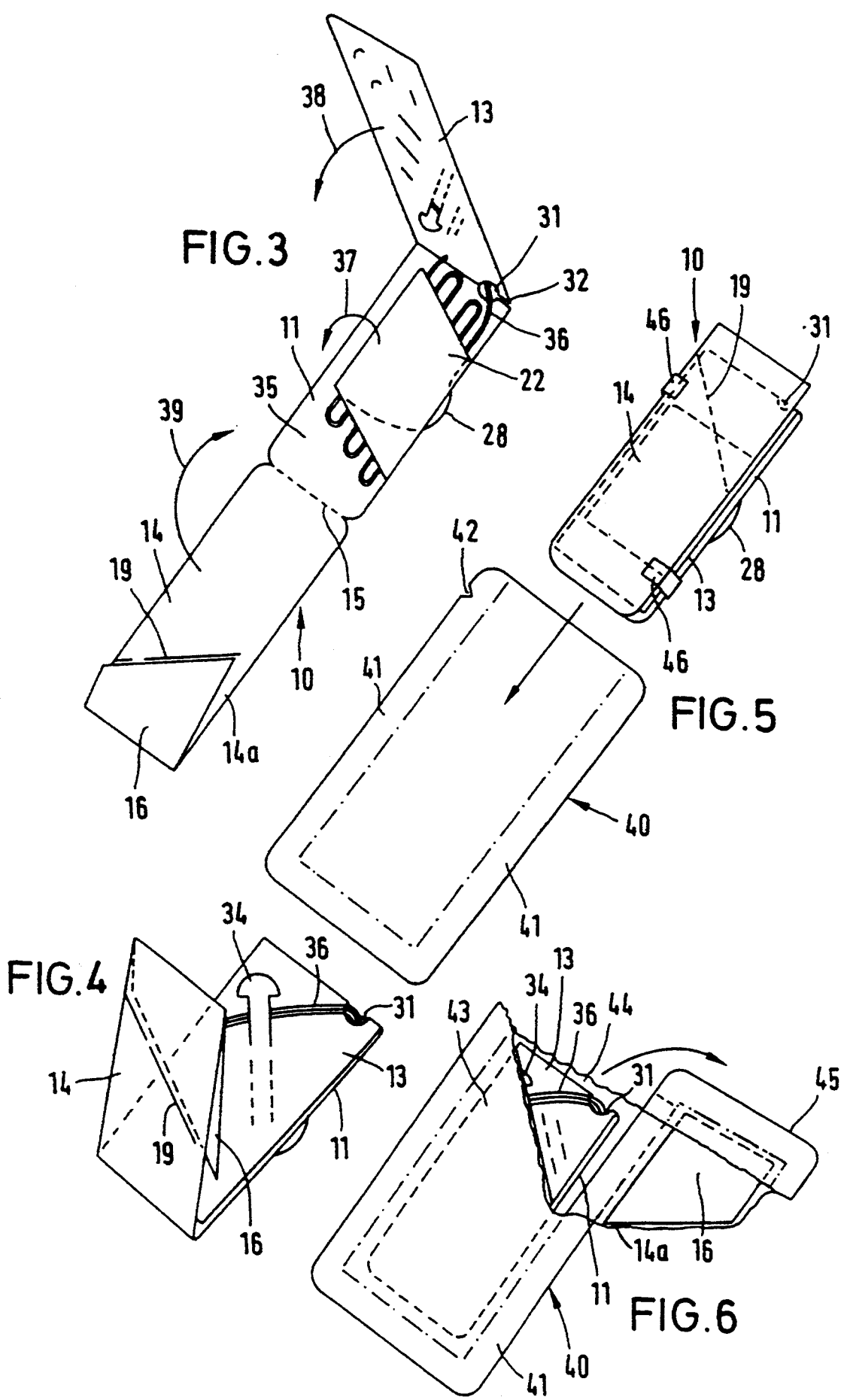

5,341,622

METHOD OF FOLDING OF PACK FOR HOLDING SUTURE MATERIAL

This is a division of application Ser. No. 07/897,276, filed on Jun. 11, 1992, now U.S. Pat. No. 5,271,494.

BACKGROUND OF THE INVENTION

1. Field of the Invention

The present invention relates to a suture material pack for surgical suture material, and in particular to a pack for holding suture material in a folding card such that it may be drawn out easily in a controlled manner.

2. Description of Related Art

U.S. Pat. No. 3,939,969 describes a suture material pack wherein the folding card consists of three elongate adjacent plates separated from each other by longitudinally extending creases. Two of these plates form holding plates that enclose the suture material and are interconnected at one of their longitudinal edges by a longitudinal crease, while the other longitudinal edges of the superimposed holding plates are connected by means of a slip-in connection. In addition to the two holding plates, a cover plate is provided that has the same length as the holding plates and is folded over the upper holding plate. The two holding plates form the receptacle for the suture material, which receptacle is open at the front ends, the suture material projecting from the end of the receptacle. The folding card is disposed in a foil sheath having a tear-off notch. Upon tearing open the foil sheath, a part of the cover plate is torn off, whereby the end of the suture material is exposed for gripping. In this suture material pack, the mechanical insertion of the suture material and the closing of the folding card pose certain problems. The suture material is laid onto the central one of the three adjacent plates, namely one of the holding plates so that, thereafter, the other holding plate and, finally, the cover plate can be folded thereon. Retaining the suture material, wound in a loop-like manner, during the closing of the folding card is difficult, since, when being closed, the plates interfere with retaining the suture material in a defined position. It is a further drawback that the suture material, which has a certain rigidity, may straighten out due to its internal stress and may come out at the front ends of the receptacle. Further, a regular pulling out of the filaments is not ensured since the same are not guided at the end of the receptacle.

U.S. Pat. No. 4,884,681 describes a suture material pack wherein the suture material is arranged on a holding plate over which flaps are folded from each side, which flaps overlap each other and cover a part of the length of the suture material. Adjoining the end of the holding plate is a cover plate also provided with laterally projecting folding flaps. The flaps of the holding plate only extend over a part of the length of the holding plate so that the suture material projects beyond the same at both ends. In such a suture material pack, the mechanical insertion of the suture material and the closing of the folding card are difficult, because the tools holding the suture material impede the closing of the folding card. The flaps connected with the holding card cannot be interlocked so that the suture material may come out unintentionally. Again, no secure and defined guiding of the filament or the filaments is ensured, when the same are drawn out.

It is an object of the present invention to provide a suture material pack that allows holding the material in a defined position, when the same is placed, and wherein the suture material is already held in place by the folding card, when the same is closed.

SUMMARY OF THE INVENTION

In the suture material pack of the present invention, the holding plates that immediately enclose the suture material are shorter than the suture material supply arranged in loops. The suture material may be held at both ends by a flap of the folding card, while gripping tools reciprocatingly arrange the rest of the suture material, consisting of one or a plurality of filaments, in meanders on the one holding plate. Thereafter, the laterally protruding other holding plate is folded over and locked in the slip-in connection. In this manner, the suture material supply is fixed between the comparatively short holding plates, while the folding card is still open. Until the slip-in connection is closed, the ends of the suture material supply can be held in place by suitable gripping tools. Thereafter, the gripping tools may release the supply since it will be held by the holding plates. The holding plates are folded over the base plate, the length of which is great enough to protrude beyond the ends of the suture material in order to protect the same.

Disposed at one of the longitudinal ends of the base plate, there is the first cover plate that forms an extension of the base plate in the longitudinal direction. The cover plate is folded over the holding plates enclosing the suture material so that the base plate and the first cover plate form the protective space for the suture material, yet do not hold and fix the suture material. The suture material is fixed by the holding plates located within the receptacle.

Preferably, the other end of the base plate is joined by a second cover plate via a second transversal crease. This second cover plate covers the first cover plate from the opposite side. The filament end projecting from the receptacle formed by the base plate and the first cover plate, is covered by the second cover plate and serves as a protective means for the filament ends and the needles possibly provided at the filaments. In order to expose this filament end when opening the pack, the second cover plate may have a tear line along which it will tear so as to expose the free filament ends or the needles.

The folding card containing the suture material is accommodated in a flat sheath which is welded along its lateral edges and may be torn open. Tearing open starts at a tear notch at the edge of the sheath. When tearing open the sheath, a part of the second cover plate is torn off along the weakened line.

In order to ensure a controlled tearing of the sheath along the weakened line of the folding card, it is provided according to a preferred development of the present invention, to partly reinforce the second cover by a folded-over reinforcing plate having a guide edge extending substantially congruently with the weakened line. Thus, the tear-off flap of the second cover plate is double-layered and is of such rigidity that the foil material of the sheath tears open in a defined manner along the border line of this flap.

BRIEF DESCRIPTION OF THE DRAWINGS

The following is a detailed description of an embodiment of the present invention in connection with the accompanying drawings.

In the Figures

FIG. 1 is a view of the blank of the folding card,

FIG. 2 illustrates the blank of FIG. 1 after the insertion of the suture material and the closing of the slip-in connection of the holding plates, FIG. 3 illustrates the manner in which the folding card is folded, FIG. 4 shows the folding card in the final state of folding, FIG. 5 shows the manner in which the folding card is inserted into the sheath, and FIG. 6 shows the tearing open of the sheath of the filament ends for taking out the filament or the filaments.

DESCRIPTION OF THE PREFERRED EMBODIMENT

As illustrated in FIG. 1, the folding card 10 consists of an integral blank of cardboard material or a plastic sheet. The folding card 10 has an elongate rectangular base plate 11, the one longitudinal end of which is joined by a first cover plate 13 via a first crease 12. The first cover plate 13 is substantially of the same shape and size as the base plate 11 so that it may be folded over the base plate which it will then cover substantially. Yet, the first cover plate 13 is slightly shorter than the base plate 11 so that the second cover plate 14 may be folded thereover, the second cover plate joining the base plate at the opposite longitudinal end thereof via a second transversal crease 15. Thus, the cover plates 13 and 14 are extensions of the base plate 11 in the longitudinal direction so that all three plates follow each other in the longitudinal direction and form an elongate strip.

Adjoining the end of the second cover plate 14 via a third transversal crease 17 is a generally triangular reinforcing plate 16. The reinforcing plate 16 has an oblique guide edge 18 at its end. When the reinforcing plate 16 is folded about the crease 17, the guide edge 18 is congruent with a weakened line 19 provided obliquely in the second cover plate and consisting of slots separated by bridges 20, 21 adapted to be ripped apart.

A first holding plate 22 projects to one side from the base plate 11, the holding plate being connected to the base plate through a longitudinal crease 23. In the center of the longitudinal crease 23, there is a slot 24, the ends of which are connected with short cuts 25 in the base plate 11.

The holding plate 22 is connected to the second holding plate 27 through a longitudinal crease 26, the second holding plate having a protruding tongue 28 at its outer edge. The two holding plates 22 and 27 are of about the same width. When the holding plate 27 is folded about the crease 26, the tongue 28 can be inserted into the slot 24 so that the holding plates are locked in an interlocked state.

The lengths of the holding plates 22 and 27 are shorter than the length of the base plate 11. More specifically, the length of the holding plates is somewhat longer than half the length of the base plate. The width of the holding plates is minimally smaller than the width of the base plate 11.

Although the holding plates 22 and 27 are substantially congruent with each other, the outer holding plate 27 has a bevel 29 having the effect that both holding plates do not overlap completely and that the slip-in connection can be opened easily if need be.

A hole 30 is provided in the center of the base plate 11 to allow a mechanical moving and guiding of the folding card 10.

In the area of the transversal crease 12 interconnecting the first cover plate 13 and the base plate 11, a hole 31 is provided that is located near one lateral edge and is meant for the passage of the filament end. A slot 32 extends from this hole 31 to the edge of the folding card. This slot 32 allows a lateral insertion of the filament end or a plurality of filament ends, even such provided with a needle, into the hole 31.

The first cover plate has a plurality of distributed cut lines 33, as well as a punched flap 34, at which the filament end or the filament ends may be fixed by insertion or by pushing the same thereunder. For example, a needle fastened at the filament end may be inserted into a slot formed by the cut lines 33. Filament ends may be inserted under the punched flap 34.

FIG. 2 illustrates the suture material 35 arranged meander-like in adjacent loops on the first holding plate 22, over which suture material the second holding plate 27 has been folded before the slip-in connection 24, 28 was closed. The suture material 35 protrudes beyond the holding plates 22, 27 at both ends. During the closing of the holding plates, it is held in place at one end or the ends by the punched flap 34 or the cut lines 33. After the closing of the holding plates, the suture material may be released, since, then, it is fixed by the holding plates, the punched flaps and the cut lines.

The suture material, consisting of a single filament or a plurality of filaments, has a protruding filament end 36 fixed by the punched flap 34 or the cut lines 33.

FIG. 3 illustrates the manner in which the two holding plates 22, 27 are folded onto the base plate 11, following the direction of the arrow 37, the subsequent folding of the first cover plate 13 thereover, following the direction of the arrow 38, and the ultimate folding of the second cover plate 14 over these, following the direction of the arrow 39. Further, the reinforcing plate 16 is folded inward or outward over the second cover plate 14. The filament end 36 is inserted from the side into the hole 31 through the slit 32.

FIG. 4 shows that a plurality of filament ends 36 lead out of the hole 31 and are fixed on the upper side of the first cover plate 13 under the punched flap 34.

According to FIG. 5, adhesive flaps 46 may be glued over the longitudinal edges of the folded folding card 10 so as to prevent unfolding. As can be seen, the second cover plate 14 protrudes beyond the base plate 11 and the first cover plate 13 towards the end where the hole 31 is provided.

The folding card 10 is inserted into the rectangular sheath 40 that consists of two multi-layered foils welded together along their edges. The weld seams are shown at 41. After the insertion of the folding card 10 into the sheath 40, sterilization is performed, whereafter the insertion opening is also closed by welding. At the one longitudinal edge of the sheath 40, a tear notch 42 is provided. In projection of the weakened line 19 of the folding card 10 inserted in the sheath 40, it is situated at the point of the greatest distance to the second transversal crease 15.

FIG. 6 illustrates the tearing open of the sheath, starting from the tear notch 42. The front foil 43 tears along the weakened line 19 of the second cover plate 14 contacting the same, while the rear foil 44 of the sheath 40 tears substantially along the transversal crease 12 of the folding card. In doing so, the flap 14a, together with the reinforcing plate 16, is torn off from the second cover plate 14 and it remains in the pocket of the torn off sheath flap 45, even without being welded to the multi-layered foil. Thereby, the filament ends 36 on the now exposed outside of the base plate 11 are exposed. These filament ends may be grasped manually so that the filament or the filament ends may be pulled from the hole 31 together or individually.

Taking out individual filaments from a multiple filament pack is possible by winding a plurality of filaments in meanders onto the holding plate 22 and by stabilizing the filament loops by the holding plate 27.

We claim:

1. A method for inserting suture material into a foldable pack comprising a plurality of plates adapted to be folded over each other to assume a folded condition, the method comprising:

providing a base plate defining a longitudinal dimension, a transversal dimension, a first end, a second end, and a side, providing a first holding plate and a second holding plate for enclosing suture material, the first holding plate defining a plurality of edges, the second holding plate defining a plurality of edges, an edge of the first holding plate being attached to an edge of the second holding plate along a crease, providing a slip-in connector associated with an edge of the first holding plate and an edge of the second holding plate for enabling a slip-in connection between an edge of the first holding plate and an edge of the second holding plate, whereby the first holding plate and the second holding plate are arrangable in a substantially interlocking relationship to thereby define a space for enclosing suture material, attaching an edge of the first holding plate to the side of the base plate along a crease that is substantially parallel to the longitudinal dimension, whereby the first and second holding plates are foldable over the base plate, the first and second holding plates being shorter than the base plate, attaching a first cover plate to the first end of the base plate along a first crease that is substantially parallel to the transversal dimension, the first cover plate and the base plate being relatively proportioned such that the first cover plate covers substantially all of the base plate when the pack is in the folded condition, fixing an end of the suture material to the first cover plate, arranging the suture material in substantially adjacent loops on the first holding plate, folding the second holding plate over the arranged suture material, establishing a slip-in connection between at least one of the edges of the first holding plate and at least one of the edges of the second holding plate, thereby locking the second holding plate over the arranged suture material, and releasing the loops of the arranged suture material, whereby at least a portion of the loops of the suture material protrude beyond at least some of the edges of the first and second holding plates.

2. The method of claim 1, comprising:

attaching a second cover plate to the second end of the base plate along a second crease that is substantially parallel to the transversal dimension.

3. The method of claim 2, comprising:

defining a substantially oblique, weakened line in the second cover plate, the weakened line and the second crease that is substantially parallel to the transversal dimension being in mutually spaced relationship and defining a point of maximum distance therebetween when the pack is in the folded condition, enclosing the pack in the folded condition with a sheath, and defining a tear notch in the sheath at a location substantially corresponding to the point of maximum distance between the weakened line and the second crease that is substantially parallel to the transversal dimension when the pack is enclosed in the sheath in the folded condition.

4. The method of claim 3, comprising at least partially reinforcing the second cover plate with a foldable reinforcing plate when the pack is in the folded condition, the reinforcing plate having a guide edge disposed substantially parallel to the weakened line when the pack is in the folded condition.

5. The method of claim 1, comprising:

arranging the base plate and the first cover plate to define an aperture for passage of a filament end disposed substantially adjacent the first crease that is substantially parallel to the transversal dimension.

6. The method of claim 5, wherein the first crease that is substantially parallel to the transversal dimension defines an end and further comprising:

providing a slot in the aperture extending towards the end of the first crease that is substantially parallel to the transversal dimension.

7. The method of claim 1, comprising:

providing the first cover plate with at least one of a cut line and a punched flap configured for holding at least one of a filament end and a needle.

* * * * *

UNITED STATES PATENT AND TRADEMARK OFFICE
CERTIFICATE OF CORRECTION

PATENT NO. : 5,341,622
DATED : AUGUST 30, 1994
INVENTOR(S) : ERICH ODERMATT, ROBERT SULZBERGER and RUDI HOFSTETTER It is certified that error appears in the above-indentified patent and that said Letters Patent is hereby corrected as shown below:

On the title page, item: 75) under Inventors, there are only two inventors listed and there are three (3) inventors, namely --ERICH ODERMATT, Schaffhausen, Switzerland; ROBERT SULZBERGER, Schaffhausen, Switzerland; and RUDI HOFSTETTER, Sempach, Switzerland--.

Signed and Sealed this

Seventh Day of March, 1995

Attest:

BRUCE LEHMAN

Attesting Officer  Commissioner of Patents and Trademarks